(12) United States Patent
Sasaoka et al.

(10) Patent No.: US 7,797,114 B2
(45) Date of Patent: Sep. 14, 2010

(54) TORQUE MEASURING APPARATUS AND ROTATION CENTER MEASURING APPARATUS

(75) Inventors: Shigefumi Sasaoka, Yokohama (JP); Hiroyuki Kondou, Tokyo (JP); Takehisa Nagano, Tokyo (JP)

(73) Assignee: Ono Sokki Co., Ltd., Yokohama-shi (JP)

( * ) Notice: Subject to any disclaimer, the term of this patent is extended or adjusted under 35 U.S.C. 154(b) by 376 days.

(21) Appl. No.: 12/014,349

(22) Filed: Jan. 15, 2008

(65) Prior Publication Data

US 2008/0172188 A1    Jul. 17, 2008

(30) Foreign Application Priority Data

Jan. 16, 2007    (JP)    ............................. 2007-007336

(51) Int. Cl.
*G01L 3/00*    (2006.01)
*G06F 15/00*    (2006.01)

(52) U.S. Cl. ........................... 702/41; 180/248; 701/69; 701/89

(58) Field of Classification Search .................. 702/33, 702/41, 113, 141, 142, 145; 73/379.01; 180/6.28, 180/6.48, 22, 248; 701/41, 69, 89
See application file for complete search history.

(56) References Cited

U.S. PATENT DOCUMENTS

| | | | |
|---|---|---|---|
| 6,208,929 B1 * | 3/2001 | Matsuno et al. ................ 701/89 |
| 6,386,308 B1 * | 5/2002 | Takahira et al. ............. 180/248 |
| 2007/0294018 A1 * | 12/2007 | Nihanda ...................... 701/69 |

FOREIGN PATENT DOCUMENTS

| | | |
|---|---|---|
| JP | 5-229439 A | 9/1993 |
| JP | 2003-81119 A | 3/2003 |

* cited by examiner

*Primary Examiner*—John H Le
(74) *Attorney, Agent, or Firm*—Westerman, Hattori, Daniels & Adrian, LLP

(57) ABSTRACT

A front wheel is placed on a lifting table, which is rotated by an actuator together with the front wheel. By rotating the lifting table by the actuator, the front wheel is rotated under constraint of a steering mechanism of an automobile. The rotation angle of an arm with respect to a base is detected by an encoder provided at an end of an extendable rod which pivotally supports the arm in a rotatable manner. The rotation angle of the base is detected by a second encoder to determine the rotation angle θ2−θ1 and rotation radius Lt of the front wheel under constraint of the steering mechanism. Based on reaction force F detected by a load cell, rotation radius Lt, and rotation angle θ2−θ1, friction torque Tt is determined.

6 Claims, 7 Drawing Sheets

TORQUE MEASURING APPARATUS AND ROTATION CENTER MEASURING APPARATUS

BACKGROUND OF THE INVENTION

1. Field of the Invention

The present invention relates to a torque measuring apparatus for measuring friction torque produced when the direction of a front wheel of an automobile is changed, and a rotation center measuring apparatus for measuring the rotation center of a front wheel of an automobile when its direction is changed.

2. Description of the Related Art

An automobile has a steering wheel and the traveling direction of the automobile is freely changed in accordance with the line of a road by the driver handling the steering wheel. As is generally known, when the steering wheel is handled, the direction of front wheels is changed in accordance with how the steering wheel is handled to change the traveling direction.

Accordingly, a channel inside the automobile that connects between the steering wheel and the front wheels has a transmission mechanism for changing the direction of the front wheels in conjunction with handling of the steering wheel. Since this transmission mechanism is mainly composed of connecting parts such as gears, the direction of wheels cannot be changed unless the steering wheel is operated with operation torque comparable to friction and the like intrinsic to the transmission mechanism. The larger the friction, greater operation torque is required and handling of the steering wheel becomes more difficult.

Accordingly, a recent automobile is provided with a power steering device in the transmission mechanism for reducing operation torque so as to provide ease of operation to drivers (reference may be made to Japanese Patent Laid-Opens No. 05-229439 and No. 2003-81119, for example).

By the way, since the friction torque and/or hysteresis characteristic (difference between leftward and rightward steering) of a steering system (from the steering wheel to wheels) of an automobile largely affects the operability of the vehicle and the feel of handling of the steering wheel, they need to be accurately measured also for management of dispersions among individual automobiles and/or trends specific to individual models (flavoring) and the like.

Figure 1:
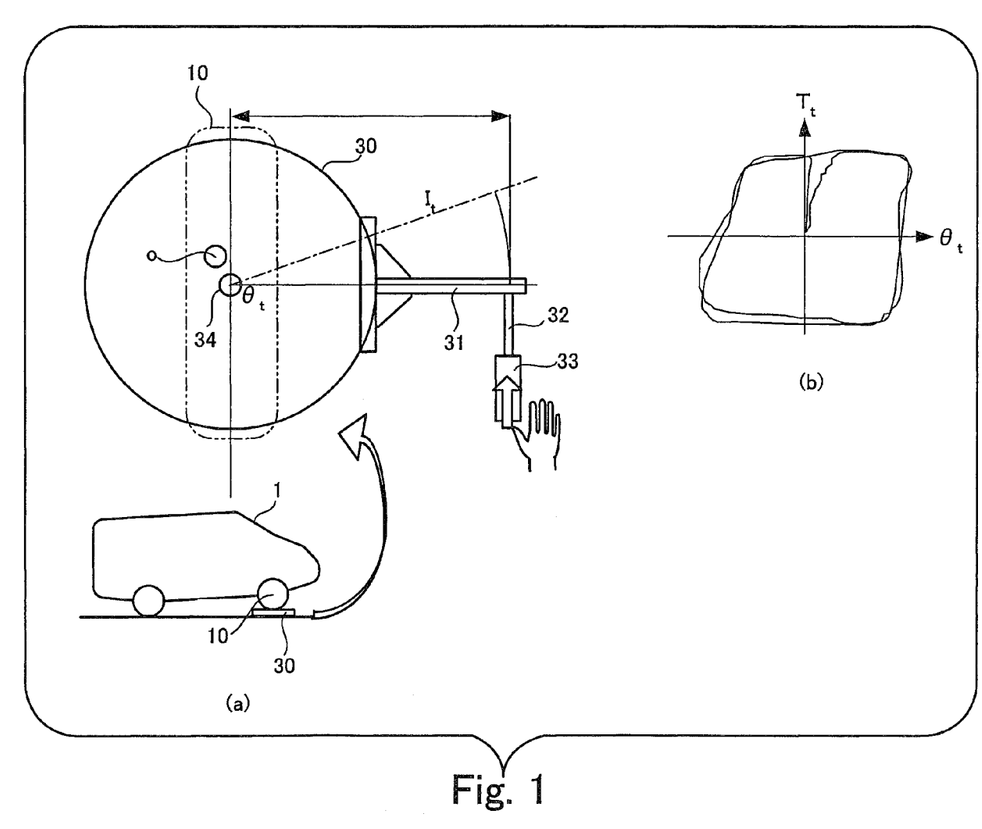
FIG. 1 shows a configuration of a measuring apparatus for measuring friction torque and a result of measurement.

FIG. 1 is a view showing a configuration of a measuring apparatus for measuring friction torque and a result of measurement. Part (a) of FIG. 1 shows the configuration of the measuring apparatus, and Part (b) of FIG. 1 shows the friction torque measured by the apparatus for each steering angle in the form of hysteresis characteristic according to the difference between leftward and rightward steering.

The configuration of the measuring apparatus will be first described with reference to Part (a) of FIG. 1.

As illustrated in the lower portion of Part (a) of FIG. 1, a front wheel 10 of an automobile 1 is placed on a turntable 30.

As illustrated in the upper portion of Part (a) of FIG. 1, an arm 31 extends from the turntable 30 with its one end fixed on the turntable, and at the other end of the extending arm 31, an operation bar 32 is provided in a direction orthogonal to the direction in which the arm 31 extends. By manually pushing and pulling the operation bar 32, it is possible to rotate the turntable 30 on which one end of the arm 31 is fixed.

At the end of the operation bar 32 on the manual operation side, there is provided a load meter 33 for measuring force while the turntable 30 is rotated by pushing and pulling the operation bar 32. At the center of the turntable 30, an angle detector 34 is provided so that measurement of the rotation angle may be measured while the turntable 30 is rotated.

Consequently, when the front wheel 10 on the turntable 30 is being rotated by pushing and pulling the operation bar 32 on the side of the load meter 33 with a hand, the force required for rotation is measured by the load meter 33 and also the rotation angle of the turntable 30 while it is being rotated by pushing and pulling the operation bar is measured by the angle detector 34 as the rotation angle of the front wheel 10. Since the length of the arm 31 shown in Part (a) of FIG. 1 is a known value, friction torque Tt can be determined for each rotation angle based on the force measured by the load meter and rotation angle θt detected by the angle detector 34. Thus, the locus of friction torque for each rotation angle in accordance with the direction of rotational operation is determined in the form of hysteresis characteristic as shown in Part (b) of FIG. 1. Part (b) of FIG. 1 shows in the form of hysteresis characteristic how friction torque changes according to the difference between leftward and rightward steering, with the lateral axis representing the rotation angle θt of the turntable and the longitudinal axis representing friction torque Tt determined from computation.

As will be seen from the configuration of Part (a) of FIG. 1, however, because the rotation center O of the wheel 10 is different from that of the turntable 30 (i.e., where the angle detector 34 is positioned), friction torque inherent in the transmission mechanism of the steering system provided in an automobile cannot be accurately determined by calculating friction torque from the rotation angle of the turntable when the front wheel 10 is fixed on the turntable 30 and is rotated with it and force measured by the load meter 33.

To resolve this, the front wheel 10 may be placed and rotated on a lifting table while moving the lifting table so that the rotation angle is detected at the rotation center of the front wheels, not the rotation center of the turntable. However, when the wheel is rotated with the lifting table, the lifting table moves along with the rotation of the front wheel due to constraint of the transmission mechanism of the steering system, thus it becomes difficult to determine the rotation center of the wheel. Friction torque cannot be accurately determined unless the rotation angle of the front wheel is determined.

SUMMARY OF THE INVENTION

The present invention has been made in view of the above circumstances and provides a torque measuring apparatus that can accurately measure friction torque and a rotation center measuring apparatus that can accurately measure the rotation center of a front wheel.

The torque measuring apparatus according to the invention is a torque measuring apparatus that measures friction torque produced when the direction of a front wheel of an automobile is changed, including:

a lifting table which lifts bearing a front wheel of an automobile;

an actuator which rotates the lifting table;

a load cell which is fixed on the actuator that measures reaction force produced when the lifting table is rotated; and a computing section that determines friction torque produced when the direction of the front wheel of the automobile is changed based on geometric factors of the actuator formed through rotation of the lifting table and force measured by the load cell.

According to the torque measuring apparatus of the invention, since the actuator rotates the front wheel by rotating the elevated lifting table while moving the lifting table, it is possible to smoothly rotate the front wheel about the rotation center of the front wheel under constraint of a transmission mechanism of a steering system provided in the automobile totally irrespective of rotation of the lifting table side.

Therefore, the computing section described above can accurately determine friction torque produced when the direction of the front wheel of the automobile is changed based on the geometric factors of the actuator which geometric factors are formed through rotation of the lifting table and reaction force measured by the load cell.

That is, the torque measuring apparatus of the present invention accurately measures friction torque by rotating the front wheel in a state in which the front wheel is constrained by the transmission mechanism of the steering system provided in the automobile about the rotation center of the steering system, by means of the actuator.

Here, the actuator preferably includes a base;

an extendable rod whose rear end is pivotally supported in the base in a rotatable manner and whose length is extended and contracted;

an arm whose rear end is pivotally supported at the front end of the extendable rod in a rotatable manner and whose front end is fixed on the lifting table;

a first encoder that is provided at the rotation center of the extendable rod with respect to the base and that detects the rotation angle of the extendable rod with respect to the base; and a second encoder that is provided at the rotation center of the arm with respect to the extendable rod and that detects the rotation angle of the arm with respect to the extendable rod, wherein the load cell is fixed on the extendable rod and measures reaction force received by the extendable rod.

Consequently, the above-described geometric factors are made up of the lengths of the extendable rod in the initial state and after its extension or contraction, the rotation angle of the extendable rod with respect to the base as detected by the first encoder, and the rotation angle of the arm with respect to the extendable rod as detected by the second encoder, and friction torque can be accurately determined based on those geometric factors and the reaction force measured by the load cell.

That is to say, given that the rotation angle of the extendable rod from the initial state as measured by the first encoder is $\theta 1$, the rotation angle of the arm from the initial state as measured by the second encoder is $\theta 2$, the length of the extendable rod in the initial state is L1, the length of the extendable rod after extension or contraction is L2, and reaction force measured by the load cell is Fa, the computing section can accurately determine friction torque Tt produced when the direction of a front wheel of the automobile is changed, according to:

$$Tt = Lt \times Fa \cos(\theta 2)$$

where Lt is the distance between the rotation center of the arm and the rotation center of the front wheel, and $$Lt = \sqrt{\{L1^2 + L2^2 - 2L1L2 \cos(\theta 1)/2(1-\cos(\theta 2-\theta 1))\}}.$$

In addition, the rotation center measuring apparatus according to the present invention is a rotation center measuring apparatus that measures the rotation center of a front wheel of an automobile when the direction of the front wheel is changed, including:

a lifting table which lifts bearing a front wheel of an automobile;

an actuator which rotates the lifting table; and a computing section that determines the rotation center of the front wheel of the automobile when the direction of the front wheel is changed based on geometric factors of the actuator formed through rotation of the lifting table.

According to the rotation center measuring apparatus of the invention, since the actuator rotates the front wheel by rotating the elevated lifting table, it is possible to smoothly rotate the front wheel centering at the rotation center of the front wheel under constraint of a transmission mechanism of a steering system provided in the automobile totally irrespective of rotation of the lifting table.

Therefore, the computing section can accurately determined the rotation center of the front wheel of the automobile when its direction is changed based on the geometric factors of the actuators which geometric factors are formed through rotation of the lifting table.

That is to say, the rotation center measuring apparatus of the invention accurately measures the rotation center of a front wheel which is constrained by the transmission mechanism of the steering system provided in the automobile.

Here, the actuator preferably includes a base;

an extendable rod whose rear end is pivotally supported in the base in a rotatable manner and whose length is extended and contracted;

an arm whose rear end is pivotally supported at the front end of the extendable rod in a rotatable manner and whose front end is fixed on the lifting table;

a first encoder that is provided at the rotation center of the extendable rod with respect to the base and that detects the rotation angle of the extendable rod with respect to the base; and a second encoder that is provided at the rotation center of the arm with respect to the extendable rod and that detects the rotation angle of the arm with respect to the extendable rod.

Consequently, the geometric factors can be made up of the lengths of the extendable rod in the initial state prior to extension or contraction and after extension or contraction, the rotation angle of the extendable rod with respect to the base as detected by the first encoder, and the rotation angle of the arm with respect to the extendable rod as detected by the second encoder, and a rotation center can be accurately calculated based on those geometric factors.

That is to say, given that the rotation angle of the extendable rod in the initial state as measured by the first encoder is $\theta 10$, the rotation angle of the arm after the extendable rod is extended or contracted as measured by the first encoder is $\theta 11$, the rotation angle of the extendable rod in the initial state as measured by the second encoder is $\theta 20$, the rotation angle of the arm after the extendable rod is extended or contracted as measured by the second encoder is $\theta 21$, the length of the extendable rod in the initial state is L1, the length of the extendable rod after extension or contraction is L2, and the distance between the rotation center of the arm and the center of the lifting table, in the initial state, is Lt0, the computing section determines the rotation center (xt, yt) of a front wheel of the automobile when the direction of the front wheel is changed, according to:

$$xt = L2 \cos(\theta 11) + Lt \cos(\theta 21) - xt0$$

$$yt = L2 \sin(\theta 11) + Lt \sin(\theta 21) - yt0$$

where Lt is a rotation radius after the extendable rod is extended/contracted, and is a value determined by:

$$Lt=\sqrt{\{L1^2+L2^2-2L1L2\cos(\theta1)/2(1-\cos(\theta2-\theta1))\}}.$$

and (xt0, yt0) are center coordinates of the lifting table, where $$xt0=L1\cos(\theta10)+Lt0\cos(\theta20)$$

$$yt0=L1\sin(\theta10)+Lt0\sin(\theta20).$$

As has been described above, according to the present invention, a measuring apparatus that can accurately measure friction torque is obtained. A measuring apparatus that can accurately measure the rotation center of a front wheel is also obtained according to the invention.

DETAILED DESCRIPTION OF THE INVENTION

An embodiment of the invention will be described with reference to the accompanied drawings.

Figure 2:
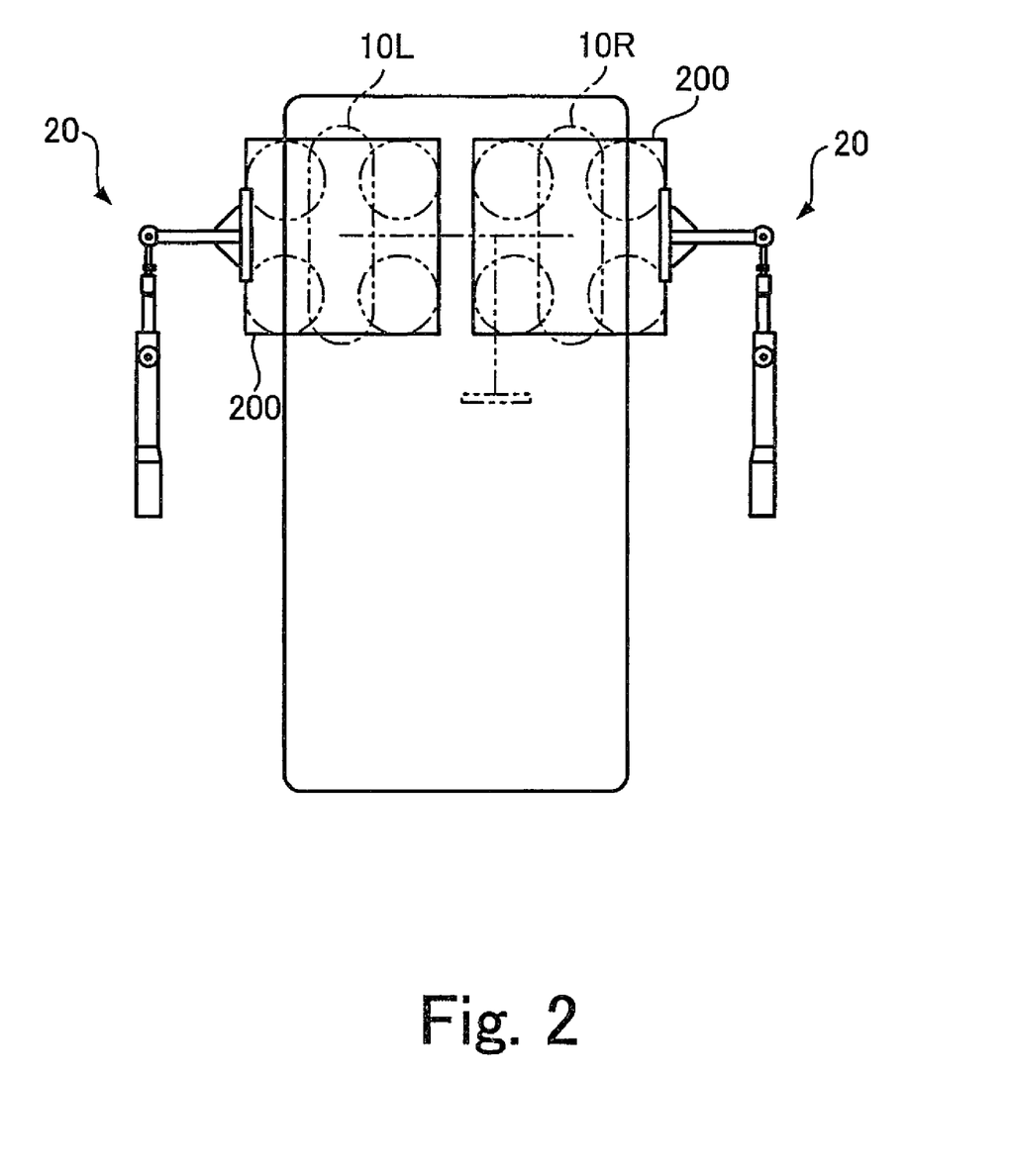
FIG. 2 illustrates a configuration of a torque measuring apparatus according to the present invention.
Figure 3:
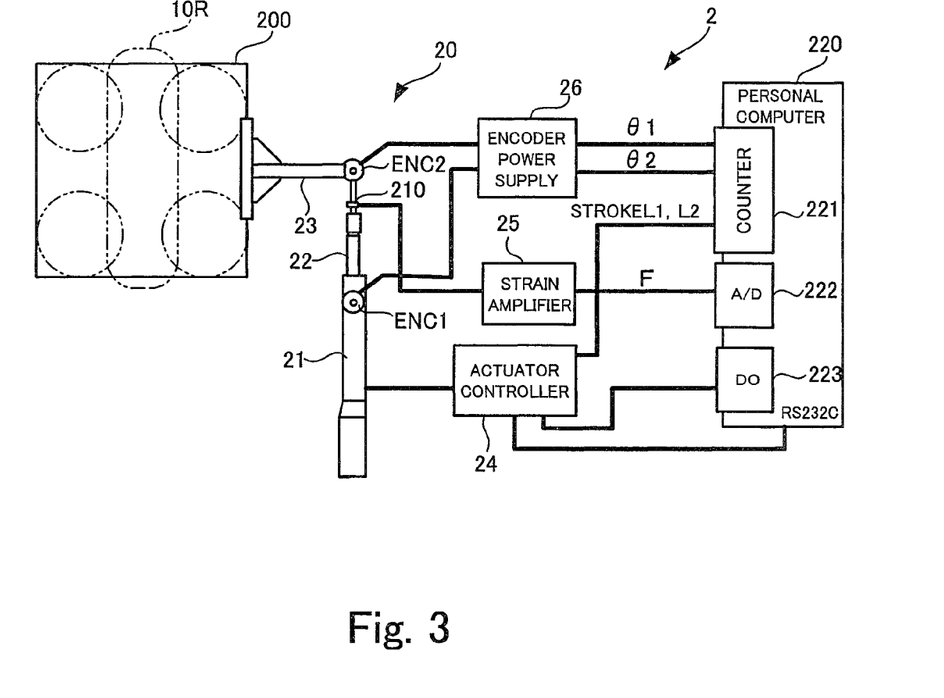
FIG. 3 illustrates a configuration of the torque measuring apparatus according to the present invention.
Figure 4:
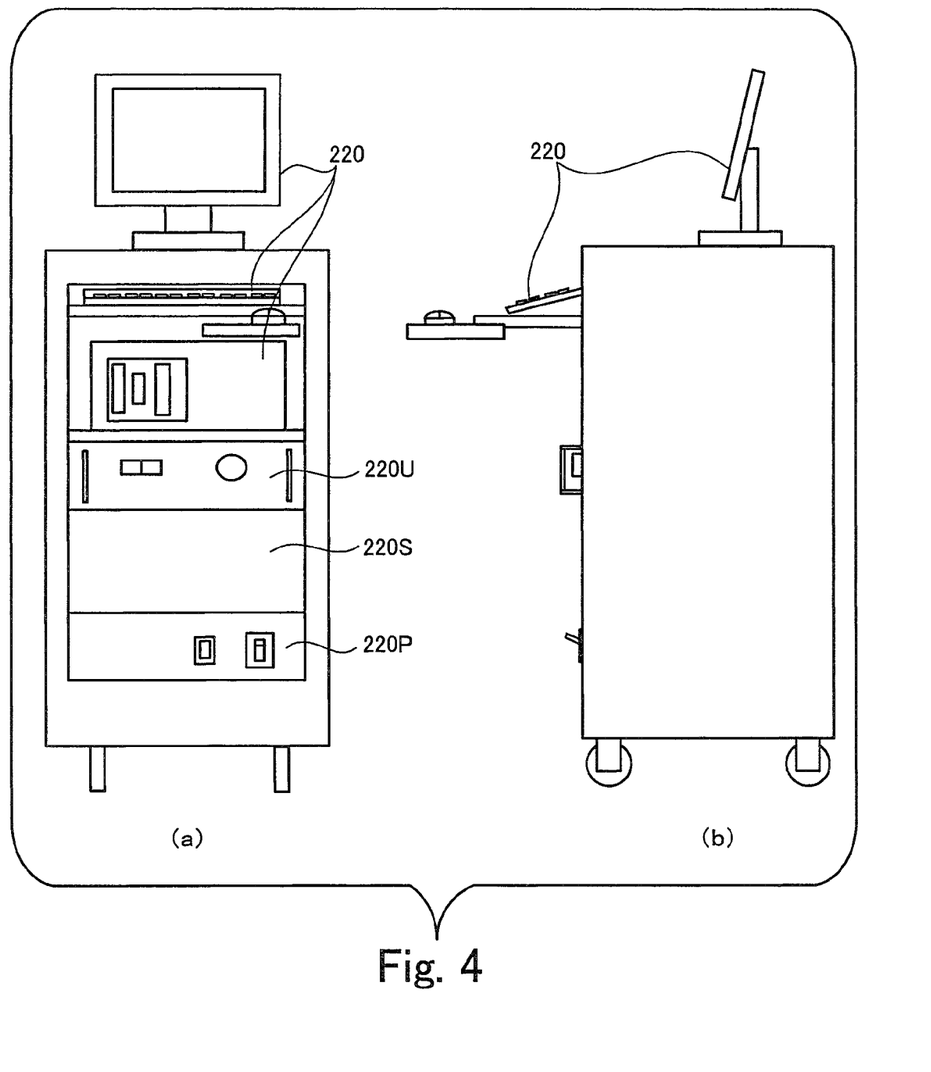
FIG. 4 shows an external appearance of a measuring apparatus 2 as contained in a control rack 2A.

FIGS. 2, 3, and 4 illustrate the configurations of the torque measuring apparatus according to the invention.

FIG. 2 is a top view of an automobile 1 placed on a lifting table 20 for showing that measurement by a measuring apparatus 2 shown in FIG. 3 is performed for both left and right front wheels 10L and 10R of the automobile 1. FIG. 2 therefore shows only actuators 20 of the torque measuring apparatus 2.

FIG. 3 shows the configuration of the measuring apparatus 2 that measures friction torque Tt of the right front wheel 10R. Similar measurement is performed also for the left front wheel 10L. FIG. 4 shows an external appearance of a control rack of the torque measuring apparatus of the invention.

Referring to FIG. 3, the configuration of the torque measuring apparatus 2 will be described.

The torque measuring apparatus 2 shown in FIG. 3 is the torque measuring apparatus 2 that measures friction torque produced when the direction of a front wheel of an automobile is changed. The torque measuring apparatus includes a lifting table 200 which lifts bearing a front wheel 10R of an automobile 10, an actuator 20 which rotates the lifting table 200, a load cell 210 fixed on the actuator 20 that measures reaction force produced when the lifting table 200 is rotated, and a personal computer (hereinafter referred to as PC) 220 which determines friction torque Tt produced when the direction of the front wheel 10R of the automobile 1 (see FIG. 2) is changed based on geometric factors of the actuator 20 which geometric factors are formed through rotation of the lifting table 200 and force measured by the load cell 210.

The actuator 20 is provided with a base 21, an extendable rod 22 whose rear end is pivotally supported in the base 21 in a rotatable manner and whose length is extended and contracted, an arm 23 whose rear end is pivotally supported at the front end of the extendable rod 22 in a rotatable manner and whose front end is fixed on the lifting table 200, a first encoder ENC 1 that is provided at the rotation center of the extendable rod 22 with respect to the base 21 and that detects the rotation angle of the extendable rod 22 with respect to the base 21, and a second encoder ENC 2 that is provided at the rotation center of the arm 23 with respect to the extendable rod 22 and that detects the rotation angle of the arm 23 with respect to the extendable rod 22. The load cell 210 shown in FIG. 3 is fixed on the extendable rod 22 and measures the reaction force received on the extendable rod 22.

The PC 220 represents a computing section according to the present invention, and it determines friction torque Tt produced when the direction of a front wheel of the automobile 1 is changed, given that the rotation angle of the extendable rod 22 from the initial state as measured by the first encoder ENC 1 is $\theta1$, the rotation angle of the arm 23 from the initial state as measured by the second encoder is $\theta2$, the length of the extendable rod 22 in the initial state is L1, the length of the extendable rod 22 after extension or contraction is L2, and reaction force measured by the load cell 210 is Fa, according to:

$$Tt=Lt\times Fa\cos(\theta2) \quad\quad \text{Equation 1}$$

where Lt is the distance between the rotation center of the arm 23 and the rotation center of the front wheel 10R, and $$Lt=\sqrt{\{L1^2+L2^2-2L1L2\cos(\theta1)/2(1-\cos(\theta2-\theta1))\}}.$$

In this example, a counter board 221, an input A/D board 222, and a DO board 223 are inserted into ISA (or PCI) slots of the PC 220. The PC 220 sets data representing a length and the direction of extension/contraction in an actuator controller 24 through the DO board 223 in accordance with an internal measurement program, and supplies a driving signal to a stepping motor not shown in the base 21 of the actuator 20 through an RS 232 port so as to extend and contract the extendable rod 22. While extending and contracting the extendable rod 22, the PC 220 receives an output signal from the load cell 210 on the input A/D board 222 through a strain amplifier 25, and also receives output signals from the two encoders, ENC 1 and ENC 2, on the counter board 221 through an encoder power supply 26 so as to calculate friction torque Tt for each steering angle $\theta t$.

In the example of FIG. 2, signals are required to be accurate for the PC 220 to calculate friction torque Tt with detection signals from ENC 1, ENC2, and the load cell 210. Therefore, the strain amplifier 25 is provided in an output stage of the load cell 210 and also the encoder power supply 26 is provided for the two encoders, ENC 1 and ENC 2, which are design ideas for enabling signals detected by the load cell 210 and the encoders ENC1, ENC2 to be transmitted to the PC 220 more accurately.

FIG. 4 shows the external appearance of the torque measuring apparatus 2 housed in the control rack 2A.

As illustrated in FIG. 4, the PC 220 is placed at the top. Provided below are a display screen of a display device for the PC 220 as well as an interface unit 220U which has thereon a indicator lamp for indicating whether the torque measuring apparatus is in operation for an operator and an emergency stop switch.

Further below, an interface unit 220S is provided that contains the strain amplifier 25, the encoder power supply 26 and so on. The actuator 20 shown in FIG. 2 is connected to the strain amplifier 25 and the encoder power supply 26 in the interface unit 220S, further to an actuator control unit 24, and wiring between the interface unit 220S and the units 221 to 223 in the slots of the PC 220 is made on the back side of the control rack 2A. At the bottom, a power supply unit 220P containing a breaker and the like is provided.

Here, description will be given of how the PC 220 of the torque measuring apparatus 2 shown in FIGS. 3 and 4 handles the geometric factors of the actuator 20 when determining friction torque Tt.

Figure 5:
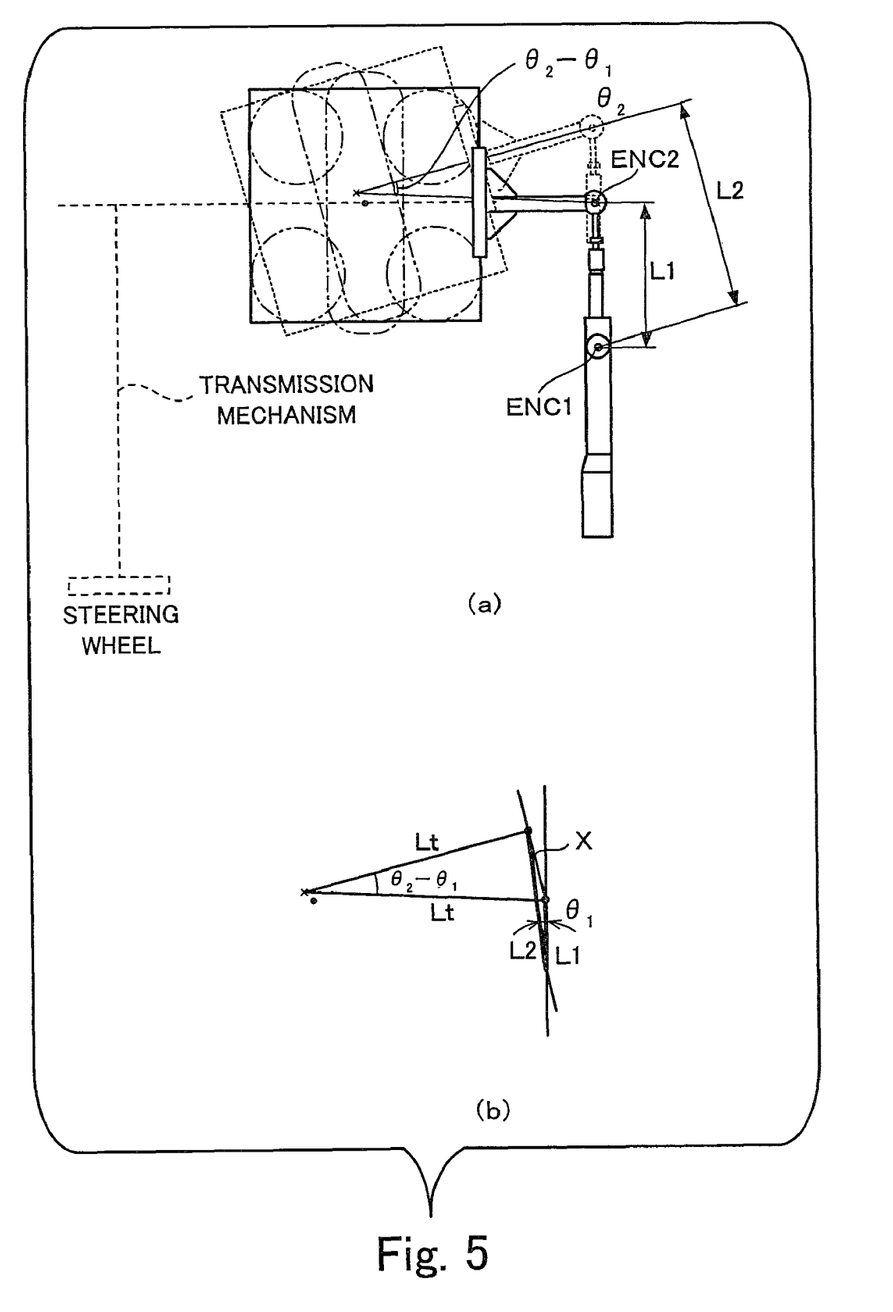
FIG. 5 illustrates geometric factors of an actuator according to the invention.

FIG. 5 illustrates the geometric factors of the actuator 20 according to the present invention.

As described above, the actuator 20 is provided with a base 21, an extendable rod 22 whose rear end is pivotally supported in the base 21 in a rotatable manner and whose length is extended and contracted, an arm 23 whose rear end is pivotally supported at the front end of the extendable rod 22 in a rotatable manner and whose front end is fixed on the lifting table 200, a first encoder ENC 1 that is provided at the rotation center of the extendable rod 22 with respect to the base 21 and that detects the rotation angle of the extendable rod 22 with respect to the base 21, and a second encoder ENC 2 that is provided at the rotation center of the arm 23 with respect to the extendable rod 22 and that detects the rotation angle of the arm 23 with respect to the extendable rod 22.

Given that the rotation angle of the extendable rod 22 from the initial state as measured by the first encoder ENC 1 is $\theta 1$, the rotation angle of the arm 23 from the initial state as measured by the second encoder ENC 2 is $\theta 2$, the length of the extendable rod 22 in the initial state is L1, the length of the extendable rod 22 after extension or contraction is L2, and reaction force measured by the load cell 210 is Fa, the PC 220 determines friction torque Tt produced when the direction of the front wheel 10R or 10L of the automobile 1 is changed according to:

$$Tt = Lt \times Fa \cos(\theta 2) \qquad \text{Equation 1}$$

where Lt is the distance between the rotation center of the arm 23 and the rotation center of the front wheel 10R, and $$Lt = \sqrt{\{L1^2 + L2^2 - 2L1L2 \cos(\theta 1)/2(1 - \cos(\theta 2 - \theta 1))\}} \qquad \text{Equation 2}$$

As will be seen also from FIG. 3, in the initial state, the base 21 does not incline and the angle between the arm 23 and the extendable rod 22 is kept almost square. Being aware of this state, the PC 220 gives an instruction to the actuator controller 24 to extend the extendable rod 22, thereby rotating the lifting table 200 together with the arm 23 to rotate the front wheel 10R under constraint of a transmission mechanism of a steering system. While the PC 220 gives an instruction to the actuator controller 24 to extend the extendable rod 22, the PC 220 obtains rotation angles from the encoders ENC1 and ENC2 at predetermined intervals, and also obtains a measurement value of reaction force from the load cell 210 and executes a geometric calculation.

While the PC 220 is extending the extendable rod 22, the end of the extendable rod 22 (where the encoder ENC2 is provided) cannot be rotated with the front wheel under constraint of the transmission mechanism of the steering system unless the base 21 is also rotated supplementarily. Therefore, the PC 220 is configured to receive angle signals from the two encoders, ENC1 and ENC2, and determine their difference to calculate the rotation angle of the front wheel.

That is, the rotation angle of the front wheel under constraint of the transmission mechanism of the steering mechanism side is an angle equal to rotation angle $\theta 2$ detected by the encoder ENC1 positioned at the end of the rod minus rotation angle $\theta 1$ detected by the encoder ENC2 positioned at the rotation center of the base 21.

The PC 220 further uses the rotation angle, the length of the extendable rod 22 according to the number of step pulses of the stepping motor in the actuator controller 24, and the cosine theorem, which is well-known for considering geometric factors, to calculate rotation radius Lt, and uses force measured by the load cell 210 to determine friction torque Tt by Equation 1.

Here, as Equation 1 can be readily understood also considering that force Fa for determining friction torque Tt represents the tangential component of a circle centered at the rotation center of the front wheel, how Equation 2 is derived will be briefly described.

First, since the end of the extendable rod 22 where the second encoder ENC2 is provided rotates centering at the rotation center of the front wheel, given that the distance of movement from the initial position of the extendable rod 22 and the position after the extendable rod 22 moves is X, X is calculated using the cosine theorem;

$$X = L1^2 + L2^2 - 2L1L2 \cos \theta 1 \qquad \text{Equation 3.}$$

Also, applying the cosine theorem to the isosceles triangle side assuming the rotation radius is Lt;

$$X = 2Lt^2 - 2Lt^2 \cos(\theta 2 - \theta 1) \qquad \text{Equation 4.}$$

Here, letting Equation 3 and Equation 4 are equal, Equation 2 is yielded.

The PC 220 included in the torque measuring apparatus 2 of the present invention determines rotation radius Lt using Equation 2, thereafter friction torque Tt using Equation 1.

In this manner, friction torque Tt is accurately calculated by the PC 220 based on both the geometric factors of the actuator 20 and reaction force measured by the load cell 210.

As described above, a torque measuring apparatus capable of accurately measuring friction torque is obtained.

Next, a rotation center measuring apparatus for determining rotation center will be described.

Figure 6:
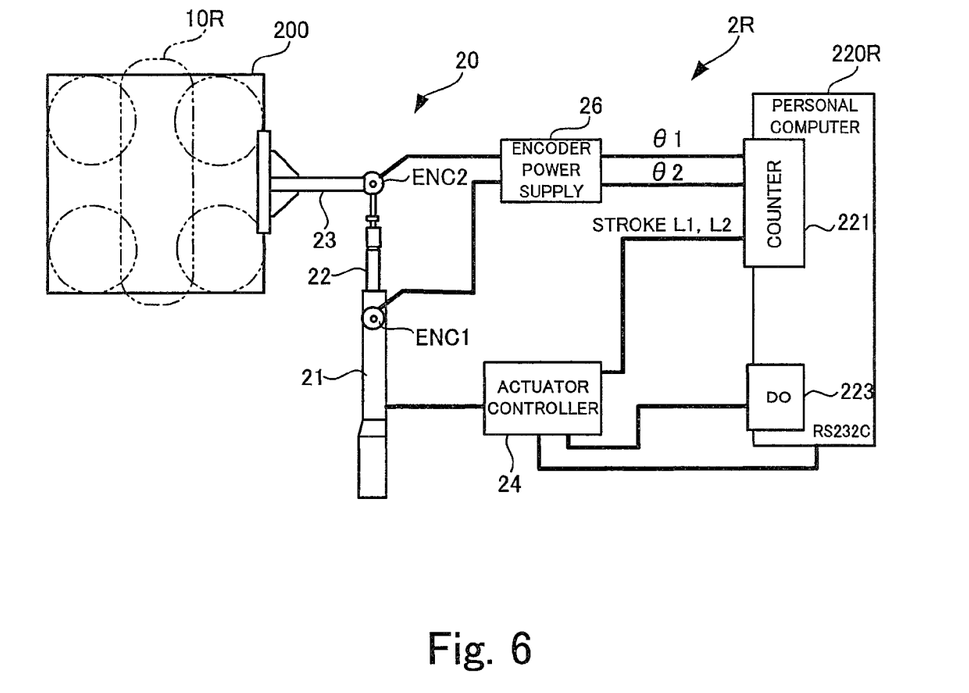
FIG. 6 shows the configuration of a rotation center measuring apparatus.

FIG. 6 illustrates the configuration of the rotation center measuring apparatus.

The configuration of a rotation center measuring apparatus 2R shown in FIG. 6 is similar to the one shown in FIG. 3 except that the load cell 210, strain amplifier 25, and the A/D unit 222 shown in FIG. 3 are removed and the program within the PC 220R is replaced with a program for calculating rotation center.

That is, because there is no need to determine friction torque, the load cell and the strain amplifier are removed and rotation center is calculated only based on the geometric factors of the actuator 20.

Figure 7:
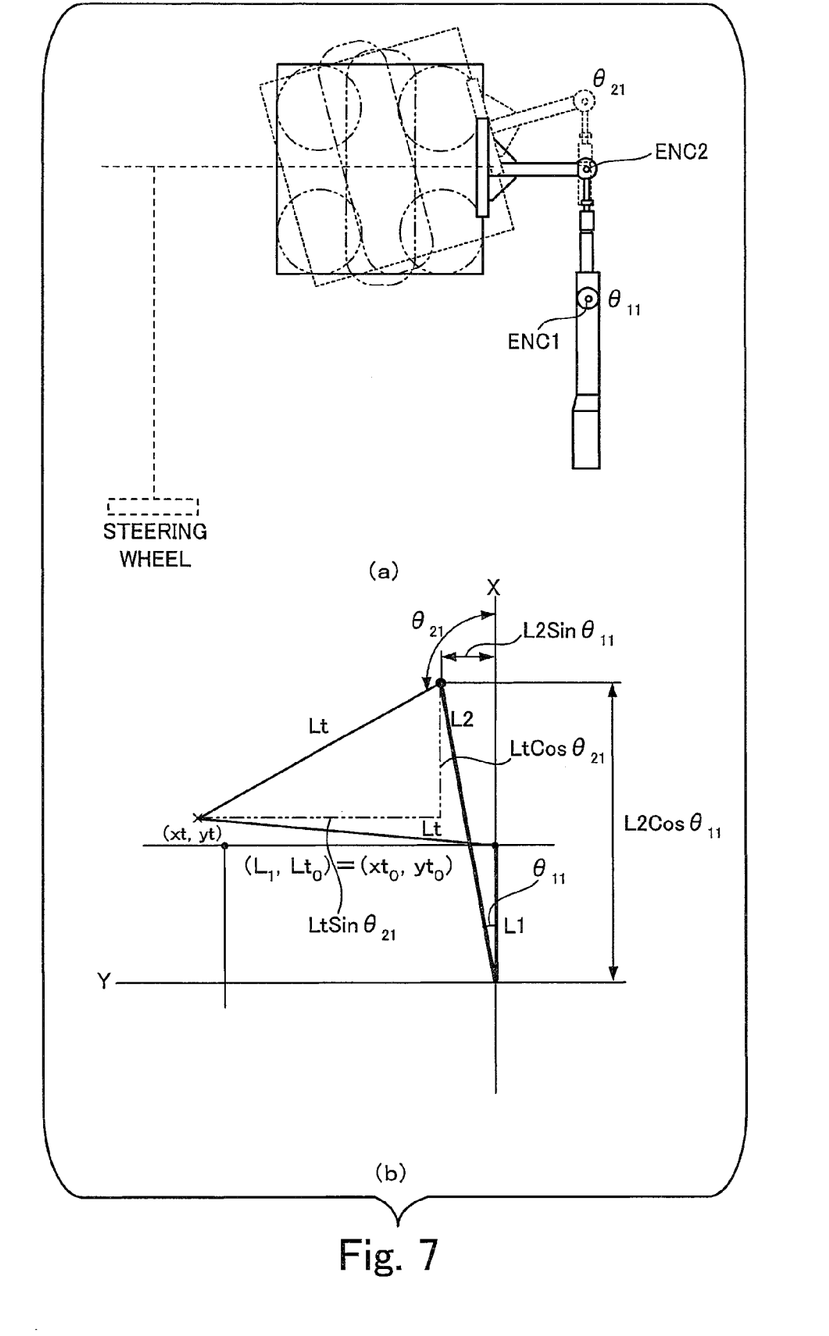
FIG. 7 illustrates the geometric factors of an actuator 20 which are used by a PC 220 provided in the rotation center measuring apparatus of the invention for determining a rotation center of a front wheel.

FIG. 7 illustrates the geometric factors of the actuator 20 which are used in determining the rotation center of the front wheel by the PC 220.

Assuming that the rotation angle of the extendable rod in the initial state as measured by the first encoder ENC 1 is $\theta 10$, the rotation angle of the arm 23 after the extendable rod 22 is extended or contracted as measured by the second encoder ENC 2 is $\theta 11$, the rotation angle of the extendable rod in the initial state as measured by the second encoder is $\theta 20$, the rotation angle of the arm after the extendable rod is extended or contracted as measured by the second encoder is $\theta 21$, the length of the extendable rod in the initial state is L1, the length of the extendable rod after extension or contraction is L2, and the distance between the rotation center of the arm and the center of the lifting table in the initial state is Lt0, the PC 220 which represents an example of computing means provided in the rotation center measuring apparatus 2 determines the rotation center (xt, yt) of a front wheel of an automobile when its direction is changed, according to:

$$xt = L2\cos(\theta 11) + Lt\cos(\theta 21) - xt0$$

$$yt = L2\sin(\theta 11) + Lt\sin(\theta 21) - yt0 \quad \text{Equation 5}$$

where Lt is the rotation radius after the extendable rod is extended/contracted, which is a value determined by:

$$Lt = \sqrt{\{L1^2 + L2^2 - 2L1L2\cos(\theta 1)/2(1-\cos(\theta 2-\theta 1))\}}$$

and (xt0, yt0) are the center coordinates of the lifting table, where $$xt0 = L1\cos(\theta 10) + Lt0\cos(\theta 20)$$

$$yt0 = L1\sin(\theta 10) + Lt0\sin(\theta 20).$$

Here, as the equations above are somewhat difficult to understand as they are, they will be specifically described by substituting numerical values into them to show specific coordinates.

For instance, assuming that the initial angle $\theta 10$ of the actuator 20 is 0° and the initial angle $\theta 20$ of the arm is 90°, let:

$$xt0 = L1 \quad yt0 = Lt0 \quad \text{Equation 6.}$$

Meanwhile, the coordinates of the rotation center of the front wheel (indicated with "x" in the figure) with the extendable rod 22 being extended and the end of the actuator 20 being under constraint of the steering mechanism side is determined in accordance with the rotation angle $\theta 11$ of the extendable rod 22 and the rotation angle $\theta 21$ of the arm 23 as:

$$xt = L2\cos(\theta 11) + Lt\cos(\theta 21) \quad \text{Equation 7}$$

$$yt = L2\sin(\theta 11) + Lt\sin(\theta 21).$$

Since $\theta 21$ is an obtuse angle, $$xt = L2\cos(\theta 11) - Lt\cos(\theta 21) \quad \text{Equation 8}$$

$$yt = L2\sin(\theta 11) + Lt\sin(\theta 21).$$

Then, the amount of movement can be easily determined by an equation that subtracts the X and Y coordinates of FIG. 6 from the X and Y coordinates of Equation 8.

When the amount of movement of the rotation center of the front wheel can be determined in this way, the rotation state of the front wheel 10R can be analytically grasped.

As described above, a measuring apparatus that can accurately measure the rotation center of a front wheel is obtained.

Although the embodiments above describe the torque measuring apparatus and the rotation center measuring apparatus separately, they can be integrated into a measuring apparatus that is capable of measuring both friction torque and rotation center concurrently by adding a program for executing calculation of rotation center described with FIG. 7 in addition to the program for calculating friction torque in the PC 220 in the configuration of FIG. 3.

What is claimed is:

1. A torque measuring apparatus that measures friction torque produced when the direction of a front wheel of an automobile is changed, comprising:
    a lifting table which lifts bearing a front wheel of an automobile;
    an actuator which rotates the lifting table;
    a load cell which is fixed on the actuator that measures reaction force produced when the lifting table is rotated; and
    a computing section that determines friction torque produced when the direction of the front wheel of the automobile is changed based on geometric factors of the actuator formed through rotation of the lifting table and force measured by the load cell.

2. The torque measuring apparatus according to claim 1, wherein
    the actuator comprises:
    a base;
    an extendable rod whose rear end is pivotally supported in the base in a rotatable manner and whose length is extended and contracted;
    an arm whose rear end is pivotally supported at the front end of the extendable rod in a rotatable manner and whose front end is fixed on the lifting table;
    a first encoder that is provided at the rotation center of the extendable rod with respect to the base and that detects the rotation angle of the extendable rod with respect to the base; and
    a second encoder that is provided at the rotation center of the arm with respect to the extendable rod and that detects the rotation angle of the arm with respect to the extendable rod, and
    the load cell is fixed on the extendable rod and measures reaction force received by the extendable rod.

3. The torque measuring apparatus according to claim 2, wherein,
    given that the rotation angle of the extendable rod from the initial state as measured by the first encoder is $\theta 1$,
    the rotation angle of the arm from the initial state as measured by the second encoder is $\theta 2$,
    the length of the extendable rod in the initial state is L1,
    the length of the extendable rod after extension or contraction is L2, and reaction force measured by the load cell is Fa,
    the computing section determines friction torque Tt produced when the direction of a front wheel of the automobile is changed, according to:

$$Tt = Lt \times Fa\cos(\theta 2)$$

where Lt is the distance between the rotation center of the arm and the rotation center of the front wheel, and $$Lt = \sqrt{\{L1^2 + L2^2 - 2L1L2\cos(\theta 1)/2(1-\cos(\theta 2-\theta 1))\}}.$$

4. A rotation center measuring apparatus that measures the rotation center of a front wheel of an automobile when the direction of the front wheel is changed, comprising:
    a lifting table which lifts bearing a front wheel of an automobile;
    an actuator which rotates the lifting table; and
    a computing section that determines the rotation center of the front wheel of the automobile when the direction of the front wheel is changed based on geometric factors of the actuator formed through rotation of the lifting table.

5. The rotation center measuring apparatus according to claim 4, wherein
    the actuator comprises:
    a base;
    an extendable rod whose rear end is pivotally supported in the base in a rotatable manner and whose length is extended and contracted;
    an arm whose rear end is pivotally supported at the front end of the extendable rod in a rotatable manner and whose front end is fixed on the lifting table;
    a first encoder that is provided at the rotation center of the extendable rod with respect to the base and that detects the rotation angle of the extendable rod with respect to the base; and a second encoder that is provided at the rotation center of the arm with respect to the extendable rod and that detects the rotation angle of the arm with respect to the extendable rod.

6. The rotation center measuring apparatus according to claim 4, wherein given that the rotation angle of the extendable rod in the initial state as measured by the first encoder is $\theta 10$, the rotation angle of the arm after the extendable rod is extended or contracted as measured by the first encoder is $\theta 11$, the rotation angle of the extendable rod in the initial state as measured by the second encoder is $\theta 20$, the rotation angle of the arm after the extendable rod is extended or contracted as measured by the second encoder is $\theta 21$, the length of the extendable rod in the initial state is L1, the length of the extendable rod after extension or contraction is L2, and the distance between the rotation center of the arm and the center of the lifting table, in the initial state, is Lt0, the computing section determines the rotation center (xt, yt) of a front wheel of the automobile when the direction of the front wheel is changed, according to:

$$xt = L2\cos(\theta 11) + Lt\cos(\theta 21) - xt0$$

$$yt = L2\sin(\theta 11) + Lt\sin(\theta 21) - yt0$$

where Lt is a rotation radius after the extendable rod is extended/contracted, and is a value determined by:

$$Lt = \sqrt{\{L1^2 + L2^2 - 2L1L2\cos(\theta 1)/2(1 - \cos(\theta 2 - \theta 1))\}}$$

and (xt0, yt0) are center coordinates of the lifting table, where $$xt0 = L1\cos(\theta 10) + Lt0\cos(\theta 20)$$

$$yt0 = L1\sin(\theta 10) + Lt0\sin(\theta 20).$$

* * * * *